United States Patent [19]

Widdig et al.

[11] 4,024,236
[45] May 17, 1977

[54] ANTHELMINTIC COMPOSITIONS AND USES EMPLOYING AMIDOPHENYLISOTHIOUREAS

[75] Inventors: Arno Widdig, Blecher; Engelbert Kühle, Berg. Gladbach; Herbert Thomas; Hans Peter Schulz, both of Wuppertal, all of Germany

[73] Assignee: Bayer Aktiengesellschaft, Germany

[22] Filed: May 19, 1975

[21] Appl. No.: 578,742

Related U.S. Application Data

[62] Division of Ser. No. 409,165, Oct. 24, 1973, abandoned.

[30] Foreign Application Priority Data

Oct. 27, 1972    Germany .......................... 2252691

[52] U.S. Cl. .............................. 424/300; 424/285
[51] Int. Cl.² ...................... A01N 9/12; A01N 9/20; A01N 9/28
[58] Field of Search .................................. 424/300

[56] References Cited

UNITED STATES PATENTS

| | | | |
|---|---|---|---|
| 3,766,243 | 10/1973 | Widdig et al. | 260/470 |
| 3,810,992 | 5/1974 | Menn | 424/300 |
| 3,843,715 | 10/1974 | Widdig et al. | 260/470 |
| 3,852,463 | 12/1974 | Widdig et al. | 424/300 |

FOREIGN PATENTS OR APPLICATIONS 1,214,415    12/1970    United Kingdom

*Primary Examiner*—Allen J. Robinson

[57] ABSTRACT

Helmintic infestations can be treated with an N-carbalkoxy-N'-(2-amido-5-alkylphenyl)-S-substituted-isothiourea. A typical embodiment is the treatment of *Bunostomum trigonocephalum* in sheep utilizing N-methoxycarbonyl-N'-(2-butyramido-5-n-butylphenyl)-S-methylisothiourea. Compositions adapted for this use are also described.

8 Claims, No Drawings

ANTHELMINTIC COMPOSITIONS AND USES EMPLOYING AMIDOPHENYLISOTHIOUREAS

This is a division of application Ser. No. 409,165, filed Oct. 24, 1973, now abandoned.

The present invention is concerned with isothioureas, a process for the production, anthelmintic compositions useful for the treatment of helmintic infections in humans and animals, and to methods of treating helmintic infections in humans and animals which comprises administering the isothioureas of the present invention to such humans and animals.

It is known in the art that the compound thiabendazole of the formula:

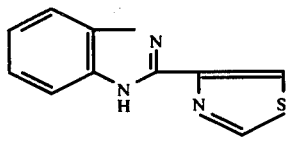

displays good anthelmintic activity. This compound is commercially available. The compounds of the present invention however are superior to this known compound as they display a substantially stronger activity against helminths than does thiabendazole.

More particularly, the present invention relates to amidophenylisothioureas of the formula:

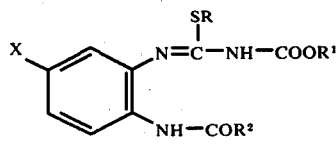

wherein
X is alkyl of 1 to 6 carbon atoms:
R is alkyl of 1 to 12 carbon atoms, cycloalkyl of 3 to 8 carbon atoms, alkenyl of 2 to 12 carbon atoms, or aralkyl of 6 to 10 carbon atoms in the aryl moiety and 1 to 4 carbon atoms in the alkyl moiety, unsubstituted or substituted in the aryl moiety by at least one substituent selected from the group consisting of alkyl of 1 to 4 carbon atoms, alkoxy of 1 to 4 carbon atoms, and halogen;
$R^1$ is alkyl of 1 to 4 carbon atoms; and
$R^2$ is hydrogen; alkyl of 1 to 18 carbon atoms unsubstituted or substituted by at least one substituent selected from the group consisting of halogen, cyano, alkoxy of 1 to 4 carbon atoms, alkoxycarbonyl of 2 to 5 carbon atoms, phenoxy, halophenoxy, alkylphenoxy of 1 to 4 carbon atoms in the alkyl moiety, and alkoxyphenoxy of 1 to 4 carbon atoms in the alkoxy moiety; cycloalkyl of 5 to 8 carbon atoms; aralkyl of 6 to 10 carbon atoms in the aryl moiety and 1 to 4 carbon atoms in the alkyl moiety, unsubstituted or substituted in the aryl moiety by at least one substituent selected from the group consisting of halogen, alkyl of 1 to 4 carbon atoms and alkoxy of 1 to 4 carbon atoms; aryl of 6 to 10 carbon atoms, unsubstituted or substituted by at least one member selected from the group consisting of alkyl of 1 to 4 carbon atoms, alkoxy of 1 to 4 carbon atoms, and halogen; or 1-furyl.

These compounds are produced by reacting a thiourea of the formula:

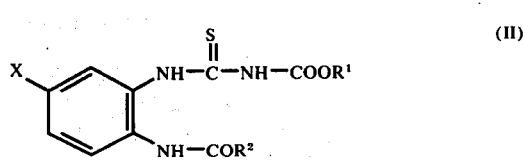

wherein
X, $R^1$ and $R^2$ are as above defined with an alkylating agent of the formula:

wherein
R is above defined, and
Y is halogen, arylsulphonyloxy, especially phenylsulphonyloxy, or alkoxysulphonyloxy of 1 to 4 carbon atoms in the alkoxy moiety,
in the presence of a base and a diluent.

The compounds of the present invention are useful for their anthelmintic activity and exhibit a broad spectrum of activity against a number of nematodes.

If for example N-(2-acetamido-5-n-butylphenyl)-N'-ethoxycarbonylthiourea, methyl iodide and sodium hydroxide are used as the starting compounds, the course of the reaction in the process of the invention can be represented by the following equation:

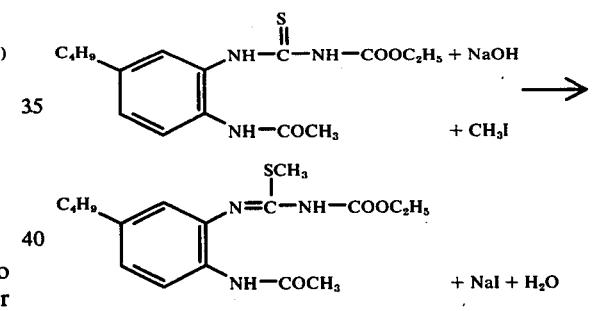

According to one embodiment of the present invention:
R is lower alkyl, cycloalkyl of 5 to 8 carbon atoms, alkenyl of 2 to 4 carbon atoms, or benzyl unsubstituted or substituted by alkyl of 1 to 4 carbon atoms, alkoxy of 1 to 4 carbon atoms, or halogen; and
$R^2$ is hydrogen; lower alkyl, unsubstituted or substituted by halogen, cyano, alkoxy of 1 to 4 carbon atoms, alkoxycarbonyl of 2 to 5 carbon atoms, phenoxy, halophenoxy, alkylphenoxy of 1 to 4 carbon atoms, or alkoxyphenoxy of 1 to 4 carbon atoms in the alkoxy moiety; cycloalkyl of 5 to 8 carbon atoms; benzyl, unsubstituted or substituted by halogen, alkyl of 1 to 4 carbon atoms or alkoxy of 1 to 4 carbon atoms; phenyl, unsubstituted or substituted by alkyl of 1 to 4 carbon atoms, alkoxy of 1 to 4 carbon atoms, or halogen; or 1-furyl.

According to another embodimeent of the present invention:
X is alkyl of 1 to 4 carbon atoms;
R is alkyl of 1 to 4 carbon atoms, alkenyl of 2 to 4 carbon atoms, cyclohexyl or benzyl;
$R^1$ is alkyl of 1 to 4 carbon atoms; and
$R^2$ is lower alkyl, cyclopentyl, cyclohexyl, phenyl, tolyl, benzyl or phenoxymethyl.

According to another embodiment of the present invention:
X is methyl, ethyl or n-butyl;
R is methyl, ethyl, isopropyl, allyl, cyclohexyl or benzyl;
$R^1$ is methyl, ethyl, isopropyl, or sec.-butyl; and
$R^2$ is methyl, ethyl, n-propyl, isopropyl, n-butyl, isobutyl, isopentyl, cyclopentyl, cyclohexyl, phenyl, p-tolyl, benzyl or phenoxymethyl.

According to another embodiment of the present invention:
X is alkyl of 1 to 4 carbon atoms;
R is alkyl of 1 to 4 carbon atoms, alkenyl of 2 to 4 carbon atoms, cyclohexyl or benzyl;
$R^1$ is alkyl of 1 to 4 carbon atoms; and
$R^2$ is lower alkyl, cyclopentyl, cyclohexyl, phenyl, benzyl or phenoxymethyl.

According to another embodiment of the present invention:
X is methyl, ethyl, or n-butyl;
R is methyl, ethyl isopropyl, allyl, cyclohexyl or benzyl;
$R^1$ is methyl, ethyl, isopropyl or sec.-butyl; and
$R^2$ is methyl, ethyl, propyl, isopropyl, butyl, isobutyl, pentyl, isopentyl, cyclopentyl, cyclohexyl, phenyl, benzyl or phenoxymethyl.

According to another embodiment of the present invention:
X is n-butyl;
R is alkyl of 1 to 4 carbon atoms, or alkenyl of 2 or 3 carbon atoms;
$R^1$ is alkyl of 1 or 2 carbon atoms; and
$R^2$ is alkyl of 1 to 4 carbon atoms or phenyl.

According to another embodiment of the present invention:
R is methyl, ethyl, isopropyl or allyl;
$R^1$ is methyl; and
$R^2$ is methyl, ethyl, propyl or phenyl.

According to the process above described, Y is preferably halogen and especially iodine.

The amidophenylthioureas (II) which are used as starting compounds in the process of the present invention are not per se known. However, they are easily producible according to German Offenlegungschrift No. 1960029 by reacting the corresponding 2-aminoaniline derivative with the appropriate isothiocyanate in the presence of an inert organic solvent at a temperature of between 0° C and 40° C.

Representative alkylating agents (III) include methyl iodide, ethyl iodide, isopropyl iodide, cyclohexyl bromide, dimethyl sulphate, toluenesulphonic acid methyl ester, allyl bromide and benzyl chloride.

Diluents suitable for use according to the process above described include water, organic solvents such as alcohol, acetone, dimethylsulphoxide, dimethylformamide and acetonitrile or mixtures of organic solvent with water.

All the bases commonly used in alkylation reaction to this type can be used in the process of the present invention. Preferred bases are potassium hydroxide, sodium hydroxide, sodium carbonate and sodium bicarbonate.

The reaction temperature may be varied over a substantial range. Preferably, the reaction temperature is between −10° C and +40° C and particularly between 0° C and 30° C.

In carrying out the process according to the invention, 1 mol of alkylating agent and 1 mol of base are preferably employed per 1 mol of amidophenlthiourea. Excess alkylating agent and base can be used without disadvantage. Working up can be carried out by adding the reaction mixture to water, filtering off the product which has precipitated, drying the product, and purifying it by recrystallization.

The following compounds are representative of those of the present invention:

N-(2-acetamido-5-methylphenyl)-N'-methoxycarbonyl-S-methylisothiourea,
N-(2-acetamido-5-ethylphenyl)-N'-methoxycarbonyl-S-methylisothiourea,
N-(2-acetamido-5-n-butylphenyl)-N'-methoxycarbonyl-S-methylisothiourea,
N-(2-acetamido-5-n-butylphenyl)-N'-ethoxycarbonyl-S-methylisothiourea,
N-(2-acetamido-5-n-butylphenyl)-N'-isopropoxycarbonyl-S-methylisothiourea,
N-(2-acetamido-5-n-butylphenyl-N'-sec-butoxycarbonyl-S-methylisothiourea,
N-(2-propionamido-5-n-butylphenyl)-N'-methoxycarbonyl-S-methylisothiourea,
N-(2-butyramido-5-n-butylphenyl)-N'-methoxycarbonyl-S-methylisothiourea,
N-(2-isobutyramido-5-n-butylphenyl)-N'-methoxycarbonyl-S-methylisothiourea,
N-(2-valeramido-5-n-butylphenyl)-N'-methoxycarbonyl-S-methylisothiourea,
N-(2-isovaleramido-5-n-butylphenyl)-N'-methoxycarbonyl-S-methylisothiourea,
N-(2-capronamido-5-n-butylphenyl)-N'-methoxycarbonyl-S-methylisothiourea,
N-(2-isocapronamido-5-n-butylphenyl)-N'-methoxycarbonyl-S-methylisothiourea,
N-(2-cyclopentanecarbonamido-5-n-butylphenyl)-N'-methoxycarbonyl-S-methylisothiourea,
N-(2-cyclohexanecarbonamido-5-n-butylphenyl)-N'-methoxycarbonyl-S-methylisothiourea,
N-(2-phenylacetamido-5-n-butylphenyl)-N'-methoxycarbonyl-S-methylisothiourea,
N-(2-phenoxyacetamido-5-n-butylphenyl)-N'-methoxycarbonyl-S-methylisothiourea,
N-(2-benzamido-5-n-butylphenyl)-N'-methoxycarbonyl-S-methylisothiourea,
N-(2-acetamido-5-n-butylphenyl)-N'-methoxycarbonyl-S-ethylisothiourea,
N-(2-acetamido-5-n-butylphenyl)-N'-methoxycarbonyl-S-isopropylisothiourea,
N-(2-acetamido-5-n-butylphenyl)-N'-methoxycarbonyl-S-allylisothiourea,
N-(2-acetamido-5-n-butylphenyl)-N'-methoxycarbonyl-S-cyclohexylisothiourea, and
N-(2-acetamido-5-n-butylphenyl)-N'-methoxycarbonyl-S-benzylisothioure.

The compounds of the present invention exhibit a broad spectrum of activity against various nematodes, for example:

1. Hookworms (for example *Bunostomum trigonocephalum*)
2. Trichostrongylides (for example *Nematospiroides dubius, Haemonchus contortus, Trichostrongylus colubriformis* and *Nippostrongylus muris*)
3. Strongylides (for example *Oesophagostomum columbianum*)
4. Rhabditides (for example *Strongyloides ratti*)

5. Eelworms (for example *TOXOCARA canis, Toxascaris leonina* and *Ascaris suum*)
6. Threadworms (for example *Aspiculuris tetraptera*)
7. Heterakides (for example *Heterakis spumosa*)
8. Filariae (for example *Litomosoides carinii* and *Dipetalonema witei*).

The anthelmintic activity of the compounds of the present invention has been established by experimental test data in animals after oral and parenteral administration to test animals heavily infected with various parasites. The dosages were well tolerated by the test animals.

The following biological data is illustrative of the activity of compounds representative of those of the present invention:

EXAMPLE A

Hookworm test/sheep

Sheep experimentally infected with *Bunostomum trigonocephalum* were treated after the end of the pre-patency period of the parasites.

The amount of active compound was administered orally as the pure active compound in gelatine capsules.

The degree of effect was determined by counting the worms expelled after the treatment and the worms which remained in the test animals, after dissection, and calculating the percentage of worms expelled.

Tables 1 to 9 which follow indicate the active compounds according to the invention and the minimum dosage which reduces the worm infection of the test animals by more than 90%: (effective minimum dose (reduced by more than 90%) in mg of active compound per kg of body weight of the test animal). In all cases, thiabendazole serves as the comparison compound.

TABLE 1

| Active compound according to the invention | Effective minimum dose (reduced >90%) in mg/kg |
| --- | --- |
| $C_4H_9$—C₆H₃(N=C(SCH₃)—NH—COOCH₃)(NH—CO—C₃H₇) (Example 1) | 25 |
| Known compound, for comparison | |
| Thiabendazole | 75 |

EXAMPLE B

Nematospiroides dubius/mouse

Mice experimentally infected with *Nematospiroides dubius* were treated after the end of the pre-patency period of the parasites. The amount of active compound was administered orally as an aqueous suspension.

The degree of effect of the preparation was determined by counting, after dissection, the worms remaining in the test animal in comparison to untreated control animals and calculating therefrom the percentage effect.

TABLE 2

| Active compound according to the invention | Effective minimum dose (reduced >90%) in mg/kg |
| --- | --- |
| $C_4H_9$—C₆H₃(N=C(SCH₃)—NH—COOCH₃)(NH—CO—C₃H₇) (Example 1) | 100 |
| $C_4H_9$—C₆H₃(N=C(SCH₃)—NH—CO—O—CH₃)(NH—CO—CH₃) (Example 3) | 250 |
| $C_4H_9$—C₆H₃(N=C(SC₂H₅)—NH—CO—O—CH₃)(NH—CO—CH₃) (Example 4) | 250 |
| $C_4H_9$—C₆H₃(N=C(S—CH₂—CH=CH₂)—NH—CO—O—CH₃)(NH—CO—CH₃) (Example 6) | 250 |

TABLE 2-continued

| Active compound according to the invention | Effective minimum dose (reduced >90%) in mg/kg |
|---|---|
| 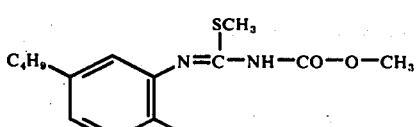 (Example 7) | 50 |
| Known compound, for comparison 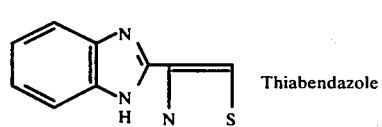 Thiabendazole | 500 |

EXAMPLE C

Stomach and intestine worm test/sheep

Sheep experimentally infected with *Haemonchus contortus* or *Trichostrongylus colubriformis* were treated after the end of the pre-patency period.

The amount of active compound was administered orally as pure active compound in gelatine capsules.

The degree of effect was determined by quantitatively counting the worm eggs excreted with the faeces before and after the treatment.

Complete cessation of the excretion of eggs after the treatment denotes that the worms have been expelled or have been damaged to the point that they can no longer produce any eggs (effective dose).

TABLE 3

| Active compound according to the invention | Parasite | Effective minimum dose (reduced >90%) in mg/kg |
|---|---|---|
| 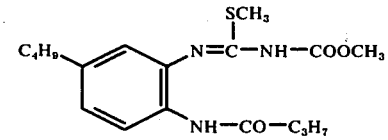 (Example 1) | *Haemonchus contortus*<br>*Trichostrongylus colubriformis* | 10<br>10 |
| 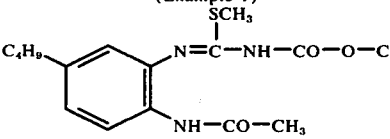 (Example 3) | *Haemonchus contortus* | 10 |
| 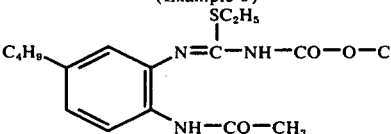 (Example 4) | *Haemonchus contortus* | 10 |
| 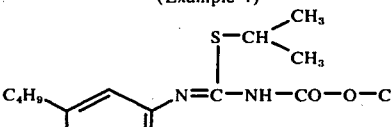 (Example 5) | *Haemonchus contortus* | 10 |
| 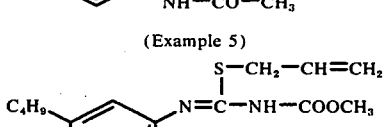 (Example 6) Known compound, for comparison | *Haemonchus contortus* | 10 |

TABLE 3-continued

| Active compound according to the invention | Parasite | Effective minimum dose (reduced >90%) in mg/kg |
|---|---|---|
| 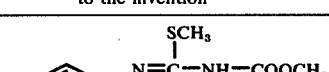 Thiabendazole | Haemonchus contortus | 50 |
| | Trichostrongylus Colubriformis | 25 |

EXAMPLE D

Knotworm test/sheep

Sheep experimentally infected with *Oesophagostomum columbianum* were treated after the end of the pre-patency period of the parasites.

The amount of active compound was administered orally as pure active compound in gelatine capsules.

The degree of effect was determined by counting the worms expelled after the treatment and the worms remaining in the test animals after dissection and calculating the percentage of worms expelled.

TABLE 4

| Active compound according to the invention | Effective minimum dose (reduced >90% in mg/kg) |
|---|---|
| (Example 1) | 10 |
| Known compound, for comparison | |
| Thiabendazole | 35 |

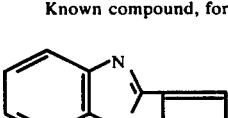

EXAMPLE E

Strongyloides ratti/rat

Rats experimentally infected with *Strongyloides ratti* were treated after the end of the pre-patency period of the parasites. The amount of active compound was administered orally as an aqueous suspension.

The degree of effect of the preparation was determined by counting, after dissection, the worms remaining in the test animal in comparison to untreated control animals and calculating therefrom the percentage of the effect.

TABLE 5

| Active compound according to the invention | Effective minimum dose (reduced 90%) in mg/kg |
|---|---|
| (Example 1) | 25 |

TABLE 5-continued

| Active compound according to the invention | Effective minimum dose (reduced 90%) in mg/kg |
|---|---|
| (Example 4) | 25 |
| (Example 7) | 10 |
| Known compound, for comparison | |
| Thiabendazole | 25 |

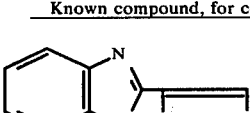

Rats experimentally infected with *Ascaris suum* were treated 2 to 4 days after infection. The amount of active compound was administered orally as an aqueous suspension.

The degree of effect of the preparation was determined by counting, after dissection, the worms remaining in the test animal in comparison to untreated control animals and calculating therefrom the percentage of the effect.

TABLE 6

| Active compound according to the invention | Effective minimum dose (reduced >90%) in mg/kg |
|---|---|
| (Example 2) | 500 |
| (Example 1) | 250 |

TABLE 6-continued

| Active compound according to the invention | Effective minimum dose (reduced >90%) in mg/kg |
|---|---|
| $C_4H_9$-C$_6$H$_3$(NH-CO-CH$_3$)-N=C(SCH$_3$)-NH-CO-O-CH$_3$ (Example 3) | 500 |
| $C_4H_9$-C$_6$H$_3$(NH-CO-CH$_3$)-N=C(S-CH(CH$_3$)$_2$)-NH-CO-O-CH$_3$ (Example 5) | 250 |
| $C_4H_9$-C$_6$H$_3$(NH-CO-CH$_3$)-N=C(S-CH$_2$-CH=CH$_2$)-NH-CO-O-CH$_3$ (Example 6) | 500 |
| $C_4H_9$-C$_6$H$_3$(NH-CO-C$_2$H$_5$)-N=C(SCH$_3$)-NH-CO-O-CH$_3$ (Example 7) | 250 |

Known compound, for comparison

| Thiabendazole | 500 |
|---|---|

EXAMPLE G

Heterakis spumose/mouse

Mice experimentally infected with *Heterakis spumosa* were treated after the end of the pre-patecy period of the parasites.

The amount of active compound was administered orally as an aqueous suspension.

The degree of effect of the preparation was determined by counting, after dissection, the worms remaining in the test animal in comparison to untreated control animals and calculating therefrom the percentage of the effect.

TABLE 7

| Active compound according to the invention | Effective minimum dose (reduced >90%) in mg/kg |
|---|---|
| $C_4H_9$-C$_6$H$_3$(NH-CO-C$_3$H$_7$)-N=C(SCH$_3$)-NH-COOCH$_3$ (Example 1) | 500 |
| $C_4H_9$-C$_6$H$_3$(NH-CO-CH$_3$)-N=C(SCH$_3$)-NH-CO-O-CH$_3$ (Example 3) | 250 |
| $C_4H_9$-C$_6$H$_3$(NH-CO-CH$_3$)-N=C(SC$_2$H$_5$)-NH-CO-O-CH$_3$ (Example 4) | 500 |
| $C_4H_9$-C$_6$H$_3$(NH-CO-C$_2$H$_5$)-N=C(SCH$_3$)-NH-CO-O-CH$_3$ (Example 7) | 250 |

Known compound, for comparison

| Thiabendazole | 500 |
|---|---|

EXAMPLE H

Aspiculuris tetraptera/mouse

Mice experimentally infected with *Aspiculuris tetraptera* were treated after the end of the pre-patency period of the parasites.

The amount of active compound was administered orally as an aqueous suspension.

The degree of effect of the preparation was determined by counting, after dissection, the worms remaining in the test animal in comparison to untreated control animals and calculating therefrom the percentage of the effect.

TABLE 8

| Active compound according to the invention | Effective minimum Dose (reduced >90%) in mg/kg |
|---|---|
| $C_4H_9$-C$_6$H$_3$(NH-CO-CH$_3$)-N=C(SCH$_3$)-NH-CO-O-CH$_3$ (Example 3) | 50 |
| $C_4H_9$-C$_6$H$_3$(NH-CO-CH$_3$)-N=C(SC$_2$H$_5$)-NH-CO-O-CH$_3$ (Example 4) | 50 |
| $C_4H_9$-C$_6$H$_3$(NH-CO-C$_2$H$_5$)-N=C(SCH$_3$)-NH-CO-O-CH$_3$ (Example 7) | 50 |

TABLE 8-continued

| Active compound according to the invention | Effective minimum Dose (reduced >90%) in mg/kg |
|---|---|
| Known compound, for comparsion  Thiabendazole | 500 |

EXAMPLE I

Trichurus muris/mouse

Mice experimentally infected with *Trichuris muris* were treated after the end of the pre-patency period of the parasites.

The amount of active compound was administered orally as an aqueous suspension.

The degree of effect of the preparation was determined by counting, after dissection, the worms remaining in the test animal in comparison to untreated control animals and calculating therefrom the percentage of the effect.

TABLE 9

| Active compound according to the invention | Effective minimum dose (reduced >90%) in mg/kg |
|---|---|
| 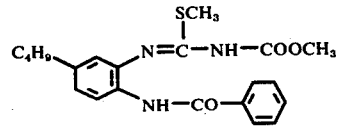 (Example 2) | 100 |
| 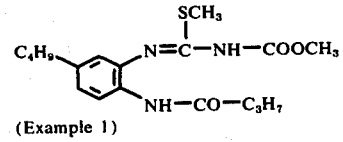 (Example 1) | 50 |
| 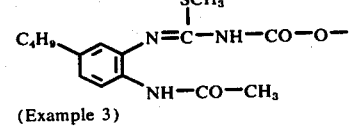 (Example 3) | 100 |
| 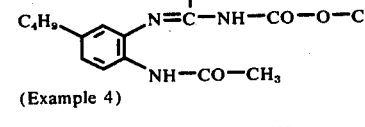 (Example 4) | 50 |
| 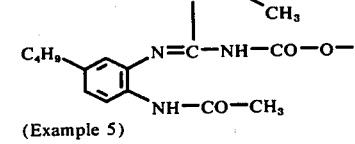 (Example 5) | 100 |
| 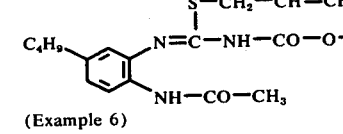 (Example 6) | 50 |

TABLE 9-continued

| Active compound according to the invention | Effective minimum dose (reduced >90%) in mg/kg |
|---|---|
| 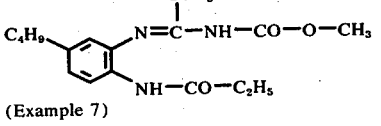 (Example 7) | 50 |
| Known compound, for comparison  Thiabendazole | inactive |

The present invention also includes pharmaceutical compositions useful for the treatment of helmintic infections in humans and animals which comprises an anthelmintically effective amount of a compound of the present invention in combination with a pharmaceutically acceptable nontoxic inert diluent or carrier.

The pharmaceutical compositions of the present invention contain a major or minor amount, e.g. 99.5% to 0.1%, preferably 90% to 0.5%, of at least one isothiourea of the present invention in combination with a pharmaceutically acceptable nontoxic inert diluent or carrier, the carrier comprising one or more solid, semi-solid or liquid diluent, filler and formulation adjuvant which is nontoxic, inert and pharmaceutically acceptable. Such pharmaceutical compositions are preferably in dosage unit form; i.e. physically discrete units containing a predetermined amount of the drug corresponding to a fraction or multiple of the dose which is calculated to produce the desired therapeutic response. The dosage units can contain one, two, three, four or more single doses or, alternatively, one-half, third or fourth of a single dose. A single dose preferably contains an amount sufficient to produce the desired therapeutic effect upon administration at one application of one or more dosage units according to a predetermined dosage regimen, usually a whole, half, third or quarter of the daily dosage administered once, twice, three or four times a day. Other therapeutic agents can also be present.

Although the dosage and dosage regimen must in each case be carefully adjusted, utilizing sound professional judgment and considering the age, weight and condition of the recipient, the route of administration and the nature and gravity of the illness, generally the dosage will be from 1 mg/kg to 100 mg/kg of body weight per day. In some instances a sufficient therapeutic effect can be obtained at a lower dose while in others, a larger dose will be required.

Oral administration can be effected utilizing solid and liquid dosage unit forms such as powders, tablets, dragees, capsules, granulates, suspensions, solutions and the like.

Powders are prepared by comminuting the compound to a suitable fine size and mixing with a similarly comminuted pharmaceutical carrier such as an edible carbohydrate as for example starch, lactose, sucrose, glucose or mannitol. Sweetening, flavoring preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agaragar, calcium carbonate or sodium carbonate can also be added to improve the availability of the medicament when the capsule is ingested.

Tablets are formulated for example by preparing a powder mixture, granulating or slugging, adding a lubricant and disintegrant and pressing into tablets. A powder mixture is prepared by mixing the compound, suitably comminuted, with a diluent or base as described above, and optionally with a binder such as carboxymethyl cellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavored aqueous sucrose solution while elixirs are prepared through the use of a nontoxic alcoholic vehicle. Suspensions can be formulated by dispersing the compound in a nontoxic vehicle. Solubilizers and emulsifiers such as ethoxylated isostearyl alcohols and polyoxyethylene sorbitol esters, preservatives, flavor additives such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a nontoxic liquid vehicle suitable for injection such as an aqueous or oleaginous medium and sterilizing the suspension or solution. Alternatively, a measured amount of the compound is placed in a vial and the vial and its contents are sterilized and sealed. An accompanying vial or vehicle can be provided for mixing prior to administration. Nontoxic salts and salt solutions can be added to render the injection isotonic. Stabilizers, preservatives and emulsifers can also be added.

Rectal administration can be effected utilizing suppositories in which the compound is admixed with low melting water soluble or insoluble solids such as polyethylene glycol, cocoa butter, higher esters as for example myristyl palmitate, or mixtures thereof.

Topical administration can be effected utilizing solid dosage unit forms such as powders or liquid or semiliquid dosage unit forms such as solutions, suspensions, ointments, pastes, creams and gels. The powders are formulated utilizing such carriers as talc, bentonite, silicic acid, polyamide powder and the like. Liquid and semiliquid formulations can utilize such carriers, in addition to those described above, as polyethylene glycol, vegetable and mineral oils, alcohols such as isopropanol and the like. Other excipients such as emulsifers, preservatives, colorants, perfumes and the like can also be present. Formulations can also be administered as an aerosol, utilizing the usual propellants such as the chlorofluorohydrocarbons.

The preferred daily dose is 50 mg to 9 g of active ingredient. Oral administration is particularly preferred.

The following non-limitative examples more particularly illustrate the present invention:

EXAMPLE 1

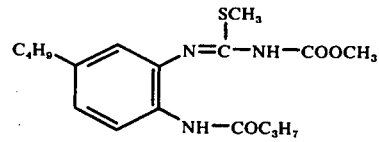

35.1 g (0.1 mol) of N-methoxycarbonyl-N'-(2-butyramido-5-n-butylphenyl)-thiourea in 200 ml of methyl alcohol are mixed with and dissolved in a solution of 5.6 g (0.1 mol) of potassium hydroxide in 10 ml of water. 15 g (about 0.1 mol) of methyl iodide are added dropwise to this mixture while stirring and cooling slightly.

After standing for 1 hour, the mixture is poured into 1 liter of water and the reaction product which precipitates is filtered off and recrystallized from a methanol/water mixture. 24 g (63% of theory) of N-methoxycarbonyl-N'-(2-butyramido-5-n-butylphenyl)-S-methylisothiourea of melting point 116° C are obtained.

The compounds of Examples 2 through 7 were prepared in a manner analogous to that of Example 1 from the reactants set forth in the table below:

| Example No. | Formula | Melting Point |
|---|---|---|
| 2 | C₄H₉—[ring]—N=C(SCH₃)—NH—COOCH₃, NH—CO—[phenyl] | 148 – 50° |
| 3 | C₄H₉—[ring]—N=C(SCH₃)—NH—COOCH₃, NH—CO—CH₃ | 143° |

-continued

| Example No. | Formula | Melting Point |
|---|---|---|
| 4 | C₄H₉—⟨ph⟩—N=C(SC₂H₅)—NH—COOCH₃ ; NH—COCH₃ | 146° C |
| 5 | C₄H₉—⟨ph⟩—N=C(SCH(CH₃)₂)—NH—COOCH₃ ; NH—COCH₃ | 140° C |
| 6 | C₄H₉—⟨ph⟩—N=C(SCH₂—CH=CH₂)—NH—COOCH₃ ; NH—COCH₃ | 107° C |
| 7 | C₄H₉—⟨ph⟩—N=C(SCH₃)—NH—COOCH₃ ; NH—COC₂H₅ | 133° C |

TABLE

| Example Nos. | Reactants |
|---|---|
| 2 | N-methoxycarbonyl-N'-(2-benzamido-5-N-butylphenyl)-thiourea and methyliodide |
| 3 | N-methoxycarbonyl-N'-(2-acetamido-5-N-butylphenyl)-thiourea and methyliodide |
| 4 | N-methoxycarbonyl-N'-(2-acetamido-5-N-butylphenyl)-thiourea and ethyliodide |
| 5 | N-methoxycarbonyl-N'-(2-acetamido-5-N-butylphenyl)-thiourea and isopropyliodide |
| 6 | N-methoxycarbonyl-N'-(2-acetamido-5-N-butylphenyl)-thiourea and allylbromide |
| 7 | N-methoxycarbonyl-N'-(2-propionamido-5-N-butylphenyl)-thiourea and dimethylsulfate |

The thiourea of the formula:

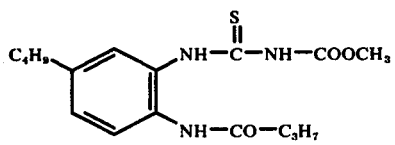

used as a starting compound in Example 1 can be produced as follows:

100 g of potassium isothiocyanate (about 1 mol) are suspended in 400 ml of dry acetone. 94.5 g (1 mol) of chloroformic acid methyl ester are added dropwise thereto, while cooling at 0°–5° C. After completion of the reaction, the mixture is stirred for a further two hours at room temperature. 117 g (0.5 mol) of 2-amino-4-n-butyl-butyranilide are then added in portions, with slight cooling. The reaction mixture is again stirred for a further 2 hours and is then poured into 5 liters of water, and the precipitate is filtered off. The precipitate which has separated out is subsequently washed with an acetone/water mixture. After drying, it is recrystallized from dioxane/water, and 110 g of N-methoxycarbonyl-N'-(2-butyramido-5-n-butylphenyl)-thiourea, representing 63% of theory, are obtained. The above mentioned substance melts, with decomposition, at 156° C.

The thioureas used as starting materials for producing the compounds of Examples 2 through 7 can be produced in an analogous manner.

7. The method according to claim 1 in which said compound is
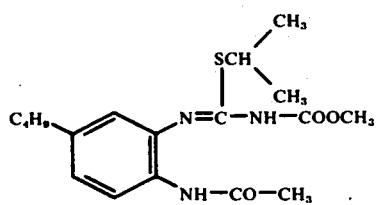
8. The method according to claim 1 in which said compound is
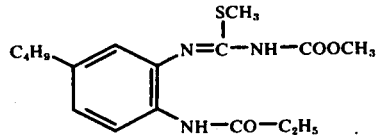

What is claimed is:

1. A method of treating helmintic infections in humans and other animals which comprises orally administering to such human or animal an anthelmintically effective amount of a compound of the formula:

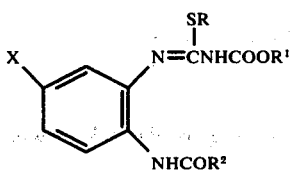

wherein X is alkyl of 1 to 4 carbon atoms;
R is alkyl of 1 to 4 carbon atoms, alkenyl of 2 to 4 carbon atoms, cyclohexyl or benzyl;
$R^1$ is alkyl of 1 to 4 carbon atoms; and
$R^2$ is alkyl of 1 to 4 carbon atoms, cyclopentyl, cyclohexyl, phenyl, benzyl or phenoxymethyl.

2. The method according to claim 1 in which said compound is

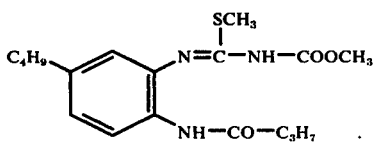

3. The method according to claim 1 in which said compound is

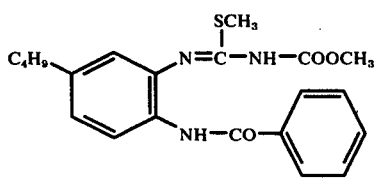

4. The method according to claim 1 in which said compound is

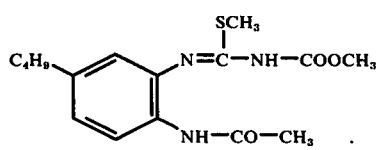

5. The method according to claim 1 in which said compound is

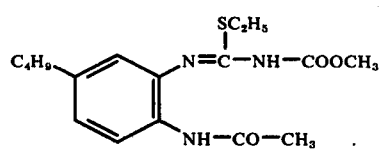

6. The method according to claim 1 in which said compound is